(12) United States Patent
Eggenweiler et al.

(10) Patent No.: US 7,491,742 B2
(45) Date of Patent: Feb. 17, 2009

(54) IMIDAZOLE DERIVATIVES AS PHOSPHODIESTERASE VII INHIBITORS

(75) Inventors: Hans-Michael Eggenweiler, Weiterstadt (DE); Rochus Jonas, Darmstadt (DE); Michael Wolf, Darmstadt (DE); Michael Gassen, Griesheim (DE); Oliver Pöschke, Wiesbaden (DE)

(73) Assignee: Merck Patent GmbH, Darmstadt (DE)

( * ) Notice: Subject to any disclaimer, the term of this patent is extended or adjusted under 35 U.S.C. 154(b) by 657 days.

(21) Appl. No.: 10/750,878

(22) Filed: Jan. 5, 2004

(65) Prior Publication Data

US 2004/0138279 A1    Jul. 15, 2004

(51) Int. Cl.
*A61K 31/415* (2006.01)
(52) U.S. Cl. .................................................. 514/397
(58) Field of Classification Search .................. 514/397
See application file for complete search history.

(56) References Cited

OTHER PUBLICATIONS

Carter et al., Chemotherapy of Cancer 2nd ed 1981.*
Christodoulos et al., Chest. 1999; 115(5): 1471.*
The abstract of Savel'ev et al. Khimiko-Farmatsevticheskii Zhurnal, 1993; 17(6):697-700.*
Hungarian Search Report for application P0203139, dated Nov. 5, 2004.
Abstract of HU Pub. No. 58337, published Feb. 28, 1992, of App. No. HU P 89 04659 A, assigned to The Boots Co. Plc.

* cited by examiner

*Primary Examiner*—San-ming Hui
(74) *Attorney, Agent, or Firm*—Millen, White, Zelano, & Branigan, P.C.

(57) ABSTRACT

Imidazole derivatives of the formula I

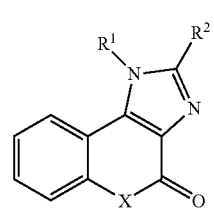

in which
$R^1$ is H, A, benzyl, indan-5-yl, 1,2,3,4-tetrahydronaphthalen-5-yl, dibenzothien-2-yl, or phenyl which is unsubstituted or mono-, di- or trisubstituted by Hal, A, A-CO—NH, benzyloxy, alkoxy, COOH or COOA,
$R^2$ is H or A,
X is O or S,
Hal is F, Cl, Br or I,
A is alkyl with 1 to 6 C atoms,
and the physiologically acceptable salts and/or solvates thereof as phosphodiesterase VII inhibitors and the use thereof for producing a pharmaceutical.

4 Claims, No Drawings

IMIDAZOLE DERIVATIVES AS PHOSPHODIESTERASE VII INHIBITORS

The invention relates to compounds of the formula I

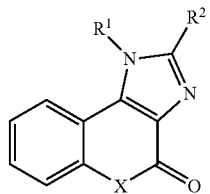

in which
R$^1$ is H, A, benzyl, indan-5-yl, 1,2,3,4-tetrahydronaphthalen-5-yl, dibenzothien-2-yl, or phenyl which is unsubstituted or mono-, di- or trisubstituted by Hal, A, A-CO—NH, benzyloxy, alkoxy, COOH or COOA,
R$^2$ is H or A,
X is O or S,
Hal is F, Cl, Br or I,
A is alkyl with 1 to 6 C atoms, and the physiologically acceptable salts and/or solvates thereof as phosphodiesterase VII inhibitors.

The invention further relates to the use of the compounds of the formula I for producing a pharmaceutical for controlling allergic disorders, asthma, chronic bronchitis, atopic dermatitis, psoriasis and other skin disorders, inflammatory disorders, autoimmune diseases such as, for example rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

Benzopyranoimidazoles are described, for example, by M. Trkovnik et al. in Org. Prep. Proced. Int. (1987), 19(6), 450-5 or by V. L. Savel'ev et al. in Khim.-Farm. Zh. (1983), 17(6), 697-700.

Benzothiopyranoimidazole derivatives are disclosed, for example, by V. L. Savel'ev et al. in Khim. Geterotsikl. Soedin. (1980), (4), 479-83.

The invention was based on the object of finding novel compounds with valuable properties, in particular those which can be used to produce pharmaceuticals.

It has been found that the compounds of the formula I and their salts have very valuable pharmacological properties while being well tolerated.

In particular, they show a specific inhibition of the "Rolipram-insensitive" cAMP phosphodiesterase (PDE VII).

The biological activity of the compounds of the formula I can be determined methods like those described, for example, by M. A. Giembycz et al. in Br. J. Pharmacol. (1996), 118, 1945-1958.

The affinity of the compounds for cAMP phosphodiesterase (PDE VII) is determined by measuring their IC$_{50}$ values (concentration of the inhibitor required to achieve 50% inhibition of enzyme activity).

The determinations were carried out by using homogenized SK-N-SH neuroblastoma cells in place of T lymphocytes, and CI-930 was employed to inhibit PDE III. The latter is a selective PDE III inhibitor (J. A. Bristol et al., J. Med. Chem. 1984, 27(9), 1099-1101).

The compounds of the formula I can be employed for treating asthmatic disorders.

The antiasthmatic effect can be determined, for example, in analogy to the method of T. Olson, Acta allergologica 26, 438-447 (1971).

Since cAMP inhibits osteoclastic cells and stimulates osteoblastic cells (S. Kasugai et al., M 681 and K. Miyamoto, M 682, in Abstracts of the American Society for Bone and Mineral Research 18th Annual Meeting, 1996), the compounds of the formula I can be employed for treating osteoporosis.

The compounds additionally show an antagonistic effect on the production of TNFα (tumour necrosis factor) and are therefore suitable for treating allergic and inflammatory disorders, autoimmune diseases such as, for example, rheumatoid arthritis, multiple sclerosis, Crohn's disease, diabetes mellitus or ulcerative colitis, transplant rejection reactions, cachexia and sepsis.

The antiinflammatory effect of the substances of the formula I and their efficacy in the treatment of, for example, autoimmune diseases such as multiple sclerosis or rheumatoid arthritis can be determined in analogy to the methods of N. Sommer et al., Nature Medicine 1, 244-248 (1995) or L. Sekut et al., Clin. Exp. Immunol. 100, 126-132 (1995).

The compounds can be employed for treating cachexia. The anticachectic effect can be tested in TNF-dependent models of cachexia (P. Costelli et al., J. Clin. Invest. 95, 2367 ff (1995); J. M. Argiles et al., Med. Res. Rev. 17, 477 ff (1997)).

PDE VII inhibitors may also inhibit the growth of tumour cells and are therefore suitable for tumour therapy (for PDE IV inhibitors, cf. D. Marko et al., Cell Biochem. Biophys. 28, 75 ff (1998)).

They can additionally be employed for the therapy of sepsis and for the treatment of memory disturbances, atherosclerosis, atopic dermatitis and AIDS, as well as for the treatment of T-cell-dependent diseases (L. Li et al., Science, 1999, 283, 848-851).

The invention further relates to the use of phosphodiesterase VII inhibitors for producing a pharmaceutical for controlling allergic disorders, asthma, chronic bronchitis, atopic dermatitis, psoriasis and other skin disorders, inflammatory disorders, autoimmune diseases such as, for example rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

The compounds of the formula I can be employed as active pharmaceutical ingredients for PDE VII inhibition in human and veterinary medicine.

A is alkyl with 1-6 C atoms and has 1, 2, 3, 4, 5 or 6 C atoms and is preferably methyl, ethyl or propyl, also preferably isopropyl, butyl, isobutyl, sec-butyl or tert-butyl, but also n-pentyl, neopentyl, isopentyl or hexyl. A is also cycloalkyl such as, for example, cyclohexyl.

Alkoxy is preferably methoxy, ethoxy, propoxy or butoxy.

Hal is preferably F or Cl.

A-CO—NH is preferably acetamido.

A base of the formula I can be converted with an acid into the relevant acid addition salt, for example by reacting equivalent amounts of the base and the acid in an inert solvent such as ethanol and subsequently evaporating. Acids particularly suitable for this reaction are those which provide physiologically acceptable salts. Thus, it is possible to use inorganic acids, for example sulfuric acid, nitric acid, hydrohalic acids such as hydrochloric acid or hydrobromic acid, phosphoric acids such as orthophosphoric acid, sulfamic acid, and organic acids, in particular aliphatic, alicyclic, araliphatic, aromatic or heterocyclic mono- or polybasic carboxylic, sulfonic or sulfuric acids, for example formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and -disulfonic acids, laurylsulfuric acid. Salts with physiologically unacceptable acids, for example picrates, can be used to isolate and/or purify the compounds of the formula I.

The invention further relates to pharmaceutical preparations comprising at least one phosphodiesterase VII inhibitor of the formula I and/or one of its physiologically acceptable salts and/or solvates for controlling allergic disorders, asthma, chronic bronchitis, atopic dermatitis, psoriasis and other skin disorders, inflammatory disorders, autoimmune diseases such as, for example rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

This usually entails the substances being administered in doses between about 1 and 500 mg, in particular between 5 and 100 mg, per dose unit. The daily dose is preferably between about 0.02 and 10 mg/kg of body weight. The specific dose for each patient depends, however, on a wide variety of factors, for example on the efficacy of the specific compound employed, on the age, body weight, general state of health, sex, on the diet, on the time and route of administration, on the rate of excretion, medicinal substance combination and severity of the particular disorder to which the therapy applies. Oral administration is preferred.

The pharmaceutical preparations can be used as pharmaceuticals in human or veterinary medicine. Suitable carriers are organic or inorganic substances which are suitable for enteral (for example oral), parenteral or topical administration and which do not react with the novel compounds, for example water, vegetable oils, benzyl alcohols, alkylene glycols, polyethylene glycols, glycerol triacetate, gelatin, carbohydrates such as lactose or starch, magnesium stearate, talc, petrolatum. Used in particular for oral administration are tablets, pills, coated tablets, capsules, powders, granules, syrups, suspensions or drops, for rectal administration are suppositories, for parenteral administration are solutions, preferably oily or aqueous solutions, also suspensions, emulsions or implants, and for topical administration are ointments, creams or dusting powders. The novel compounds can also be lyophilized and the resulting lyophilizates be used for example for producing products for injection. The indicated preparations can be sterilized and/or comprise excipients such as lubricants, preservatives, stabilizers and/or wetting agents, emulsifiers, salts to influence the osmotic pressure, buffer substances, colorants, flavourings and/or several other active ingredients, for example one or more vitamins.

The invention particularly relates to the compounds of the formula I listed in the following examples and their physiologically acceptable salts and/or solvates as PDE VII inhibitors, and to the use thereof for producing a pharmaceutical for controlling allergic disorders, asthma, chronic bronchitis, atopic dermatitis, psoriasis and other skin disorders, inflammatory disorders, autoimmune diseases such as, for example rheumatoid arthritis, multiple sclerosis, Crohn's disease, diabetes mellitus or ulcerative colitis, osteoporosis, transplant rejection reactions, cachexia, tumour growth or tumour metastases, sepsis, memory disturbances, atherosclerosis and AIDS.

EXAMPLES

1-Phenyl-[1]benzopyrano[3,4-d]imidazol-4-(1H)-one,
1-Benzyl-[1]benzopyrano[3,4-d]imidazol-4-(1H)-one,
1-Cyclohexyl-[1]benzopyrano[3,4-d]imidazol-4-(1H)-one,
1-Cyclopentyl-[1]benzopyrano[3,4-d]imidazol-4-(1H)-one,
1-Butyl-[1]benzopyrano[3,4-d]imidazol-4-(1H)-one,
1-Isopropyl-[1]benzopyrano[3,4-d]imidazol-4-(1H) -one,
1-Propyl-[1]benzopyrano[3,4-d]imidazol-4-(1H)-one,
1-Ethyl-[1]benzopyrano[3,4-d]imidazol-4-(1H)-one,
1-Methyl-[1]benzopyrano[3,4-d]imidazol-4-(1H)-one,
[1]Benzopyrano[3,4-d]imidazol-4-(1H)-one,
2-Methyl-[1]benzopyrano[3,4-d]imidazol-4-(1H)-one,
1-Phenyl-[1]benzothiopyrano[3,4-d]imidazol-4-(1H)-one,
1-Benzyl-[1]benzothiopyrano[3,4-d]imidazol-4-(1H)-one,
1-Cyclohexyl-[1]benzothiopyrano[3,4-d]imidazol-4-(1H)-one,
1-Cyclopentyl-[1]benzothiopyrano[3,4-d]imidazol-4-(1H)-one,
1-Butyl-[1]benzothiopyrano[3,4-d]imidazol-4-(1H)-one,
1-Isopropyl-[1]benzothiopyrano[3,4-d]imidazol-4-(1H)-one,
1-Propyl-[1]benzothiopyrano[3,4-d]imidazol-4-(1H)-one,
1-Ethyl-[1]benzothiopyrano[3,4-d]imidazol-4-(1H)-one,
1-Methyl-[1]benzothiopyrano[3,4-d]imidazol-4-(1H) -one,
[1]Benzothiopyrano[3,4-d]imidazol-4-(1H)-one,
2-Methyl-[1]benzothiopyrano[3,4-d]imidazol-4-(1H)-one,
1-(2-Chlorophenyl-[1]benzopyrano[3,4-d]imidazol-4-(1H)-one,
1-(4-Methyl-phenyl)-[1]benzopyrano[3,4-d]imidazol-4-(1H)-one,
1-(4-Fluorophenyl)-[1]benzopyrano[3,4-d]imidazol-4-(1H)-one,
1-(2,4-Dimethyl-phenyl)-[1]benzopyrano[3,4-d]imidazol-4-(1H)-one,
1-(3-Chlorophenyl)-[1]benzopyrano[3,4-d]imidazol-4-(1H)-one,
1-(2,4-Dichlorophenyl)-[1]benzopyrano[3,4-d]imidazol-4-(1H)-one,
1-(2,5-Dichlorophenyl)-[1]benzopyrano[3,4-d]imidazol-4-(1H)-one,
1-(4-Acetamido-phenyl)-[1]benzopyrano[3,4-d]imidazol-4-(1H)-one,
1-(2-Fluorophenyl)-[1]benzopyrano[3,4-d]imidazol-4-(1H)-one,
1-(3-Fluorophenyl)-[1]benzopyrano[3,4-d]imidazol-4-(1H)-one,
1-(2-Benzyloxy-phenyl)-[1]benzopyrano[3,4-d]imidazol-4-(1H)-one,
1-(2,6-Dimethyl-phenyl)-[1]benzopyrano[3,4-d]imidazol-4-(1H)-one,
1-(Indan-5-yl)-[1]benzopyrano[3,4-d]imidazol-4-(1H)-one,
1-(2-Methoxy-phenyl)-[1]benzopyrano[3,4-d]imidazol-4-(1H)-one,
1-(2,3-Dimethyl-phenyl)-[1]benzopyrano[3,4-d]imidazol-(1H)-4-one,
1-(2,3-Dichlorophenyl)-[1]benzopyrano[3,4-d]imidazol-4-(1H)-one,
1-(3-Chloro-4-methyl-phenyl)-[1]benzopyrano[3,4-d]imidazol-4-(1H)-one,
1-(2,5-Dimethyl-phenyl)-[1]benzopyrano[3,4-d]imidazol-4-(1H)-one, 1-(4-Chlorophenyl)-[1]benzopyrano[3,4-d]imidazol-4-(1H)-one,
1-(1,2,3,4-Tetrahydronaphthalen-5-yl)-[1]benzopyrano-[3,4-d]imidazol-4-(1H)-one,
1-(Dibenzothien-2-yl)-[1]benzopyrano[3,4-d]imidazol-4-(1H)-one,
1-(3-Methoxy-phenyl)-[1]benzopyrano[3,4-d]imidazol-4-(1H)-one,
1-(4-Carboxy-2-methyl-phenyl)-[1]benzopyrano[3,4-d]imidazol-4-(1H)-one, The following examples relate to pharmaceutical preparations:

Example A

Vials

A solution of 100 g of a phosphodiesterase VII inhibitor of the formula I and 5 g of disodium hydrogen phosphate in 3 l of double-distilled water is adjusted to pH 6.5 with 2 N hydrochloric acid, sterilized by filtration, dispensed into vials, lyophilized under sterile conditions and sealed sterile. Each vial contains 5 mg of active ingredient.

Example B

Suppositories

A mixture of 20 g of a phosphodiesterase VII inhibitor of the formula I with 100 g of soya lecithin and 1400 g of cocoa butter is melted, poured into moulds and left to cool. Each suppository contains 20 mg of active ingredient.

Example C

Solution

A solution is prepared from 1 g of a phosphodiesterase VII inhibitor of the formula I, 9.38 g of $NaH_2PO_4.2H_2O$, 28.48 g of $Na_2HPO_4.12H_2O$ and 0.1 g of benzalkonium chloride in 940 ml of double-distilled water. The pH is adjusted to 6.8, the volume is made up to 1 l, and the solution is radiation-sterilized. The solution can be used in the form of eyedrops.

Example D

Ointment 500 mg of a phosphodiesterase VII inhibitor of the formula I are mixed with 99.5 g of petrolatum under aseptic conditions.

Example E

Tablets

A mixture of 1 kg of phosphodiesterase VII inhibitor of the formula I, 4 kg of lactose, 1.2 kg of potato starch, 0.2 kg of talc and 0.1 kg of magnesium stearate is compressed to tablets in a conventional way so that each tablet contains 10 mg of active ingredient.

Example F

Coated Tablets

Tablets are compressed in analogy to Example E and are then coated in a conventional way with a coating consisting of sucrose, potato starch, talc, tragacanth and colorant.

Example G

Capsules 2 kg of phosphodiesterase VII inhibitor of the formula I are packed in a conventional way into hard gelatin capsules so that each capsule contains 20 mg of the active ingredient.

Example H

Ampoules

A solution of 1 kg of phosphodiesterase VII inhibitor of the formula I in 60 l of double-distilled water is sterilized by filtration, dispensed into ampoules, lyophilized under sterile conditions and sealed sterile. Each ampoule contains 10 mg of active ingredient.

Example I

Inhalation Spray 14 g of phosphodiesterase VII inhibitor of the formula I are dissolved in 10 l of isotonic NaCl solution, and the solution is dispensed into commercial spray vessels with a pump mechanism. The solution can be sprayed into the mouth or nose. One spray actuation (about 0.1 ml) corresponds to a dose of about 0.14 mg.

The invention claimed is:

1. A method of treating allergic disorders, asthma, chronic bronchitis, atopic dermatitis, psoriasis, inflammatory disorders, autoimmune diseases, osteoporosis, transplant rejection reactions, cachexia, tumor growth, tumor metastases, sepsis, or atherosclerosis comprising administering, to a host in need thereof, an effective amount of a compound of formula I

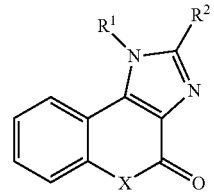

in which
$R^1$ is H, A, benzyl, indan-5-yl, 1,2,3,4-tetrahydronaphthalen-5-yl, dibenzothien-2-yl, or phenyl which is unsubstituted or mono-, di- or trisubstituted by Hal, A, A-CO—NH, benzyloxy, alkoxy, COOH or COOA,
$R^2$ is H or A,
X is O or S,
Hal is F, Cl, Br or I,
A is alkyl with 1 to 6 C atoms,
or a physiologically acceptable salt or solvate thereof.

2. A method according to claim 1, wherein the autoimmune disorder is rheumatoid arthritis, multiple sclerosis, Crohn's disease, diabetes mellitus, ulcerative colitis or AIDS.

3. A method according to claim 1, wherein the compound of formula I is
1-Phenyl-[1]benzopyrano[3,4-d]imidazol-4-(1H)-one,
1-Benzyl-[1]benzopyrano[3,4-d]imidazol-4-(1H)-one,
1-Cyclohexyl-[1]benzopyrano[3,4-d]imidazol-4-(1H)-one, 1-Cyclopentyl-[1]benzopyrano[3,4-d]imidazol-4-(1H)-one,
1-Butyl-[1]benzopyrano[3,4-d]imidazol-4-(1H)-one,
1-Isopropyl-[1]benzopyrano[3,4-d]imidazol-4-(1H)-one,
1-Propyl-[1]benzopyrano[3,4-d]imidazol-4-(1H)-one,
1-Ethyl-[1]benzopyrano[3,4-d]imidazol-4-(1H)-one,
1-Methyl-[1]benzopyrano[3,4-d]imidazol-4-(1H)-one,
[1]Benzopyrano[3,4-d]imidazol-4-(1H)-one,
2-Methyl-[1]benzopyrano[3,4-d]imidazol-4-(1H)-one,
1-Phenyl-[1]benzothiopyrano[3,4-d]imidazol-4-(1H)-one,
1-Benzyl-[1]benzothiopyrano[3,4-d]imidazol-4-(1H)-one,
1-Cyclohexyl-[1]benzothiopyrano[3,4-d]imidazol-4-(1H)-one,
1-Cyclopentyl-[1]benzothiopyrano[3,4-d]imidazol-4-(1H)-one,
1-Butyl-[1]benzothiopyrano[3,4-d]imidazol-4-(1H)-one,
1-Isopropyl-[1]benzothiopyrano[3,4-d]imidazol-4-(1H)-one,
1-Propyl-[1]benzothiopyrano[3,4-d]imidazol-4-(1H)-one,
1-Ethyl-[1]benzothiopyrano[3,4-d]imidazol-4-(1H)-one,
1-Methyl-[1]benzothiopyrano[3,4-d]imidazol-4-(1H)-one,
[1]Benzothiopyrano[3,4-d]imidazol-4-(1H)-one,
2-Methyl-[1]benzothiopyrano[3,4-d]imidazol-4-(1H)-one,
1-(2-Chlorophenyl-[1]benzopyrano[3,4-d]imidazol-4-(1H)-one,
1-(4-Methyl-phenyl)-[1]benzopyrano[3,4-d]imidazol-4-(1H)-one,
1-(4-Fluorophenyl)-[1]benzopyrano[3,4-d]imidazol-4-(1H)-one,
1-(2,4-Dimethyl-phenyl)-[1]benzopyrano[3,4-d]imidazol-4-(1H)-one,
1-(3-Chlorophenyl)-[1]benzopyrano[3,4-d]imidazol-4-(1H)-one,
1-(2,4-Dichlorophenyl)-[1]benzopyrano[3,4-d]imidazol-4-(1H)-one,
1-(2,5-Dichlorophenyl)-[1]benzopyrano[3,4-d]imidazol-4-(1H)-one,
1-(4-Acetamido-phenyl)-[1]benzopyrano[3,4-d]imidazol-4-(1H)-one,
1-(2-Fluorophenyl)-[1]benzopyrano[3,4-d]imidazol-4-(1H)-one,
1-(3-Fluorophenyl)-[1]benzopyrano[3,4-d]imidazol-4-(1H)-one,
1-(2-Benzyloxy-phenyl)-[1]benzopyrano[3,4-d]imidazol-4-(1H)-one,
1-(2,6-Dimethyl-phenyl)-[1]benzopyrano[3,4-d]imidazol-4-(1H)-one,
1-(Indan-5-yl)-[1]benzopyrano[3,4-d]imidazol-4-(1H)-one,
1-(2-Methoxy-phenyl)-[1]benzopyrano[3,4-d]imidazol-4-(1H)-one,
1-(2,3-Dimethyl-phenyl)-[1]benzopyrano[3,4-d]imidazol-(1H)-4-one,
1-(2,3-Dichlorophenyl)-[1]benzopyrano[3,4-d]imidazol-4-(1H)-one,
1-(3-Chloro-4-methyl-phenyl)-[1]benzopyrano[3,4-d]imidazol-4-(1H)-one,
1-(2,5-Dimethyl-phenyl)-[1]benzopyrano[3,4-d]imidazol-4-(1H)-one,
1-(4-Chlorophenyl)-[1]benzopyrano[3,4-d]imidazol-4-(1H)-one,
1-(1,2,3,4-Tetrahydronaphthalen-5-yl)-[1]benzopyrano-[3,4-d]imidazol-4-(1H)-one,
1-(Dibenzothien-2-yl)-[1]benzopyrano[3,4-d]imidazol-4-(1H)-one,
1-(3-Methoxy-phenyl)-[1]benzopyrano[3,4-d]imidazol-4-(1H)-one, or
1-(4-Carboxy-2-methyl-phenyl)-[1]benzopyrano[3,4-d]imidazol-4-(1H)-one.

4. A method according to claim 2, wherein the compound of formula I is
1-Phenyl-[1]benzopyrano[3,4-d]imidazol-4-(1H)-one,
1-Benzyl-[1]benzopyrano[3,4-d]imidazol-4-(1H)-one,
1-Cyclohexyl-[1]benzopyrano[3,4-d]imidazol-4-(1H)-one,
1-Cyclopentyl-[1]benzopyrano[3,4-d]imidazol-4-(1H)-one,
1-Butyl-[1]benzopyrano[3,4-d]imidazol-4-(1H)-one,
1-Isopropyl-[1]benzopyrano[3,4-d]imidazol-4-(1H)-one,
1-Propyl-[1]benzopyrano[3,4-d]imidazol-4-(1H)-one,
1-Ethyl[1]benzopyrano[3,4-d]imidazol-4-(1H)-one,
1-Methyl-[1]benzopyrano[3,4-d]imidazol-4-(1H)-one,
[1]Benzopyrano[3,4-d]imidazol-4-(1H)-one,
2-Methyl-[1]benzopyrano[3,4-d]imidazol-4-(1H)-one,
1-Phenyl-[1]benzothiopyrano[3,4-d]imidazol-4-(1H)-one,
1-Benzyl-[1]benzothiopyrano[3,4-d]imidazol-4-(1H)-one,
1-Cyclohexyl-[1]benzothiopyrano[3,4-d]imidazol-4-(1H)-one,
1-Cyclopentyl-[1]benzothiopyrano[3,4-d]imidazol-4-(1H)-one,
1-Butyl-[1]benzothiopyrano[3,4-d]imidazol-4-(1H)-one,
1-Isopropyl-[1]benzothiopyrano[3,4-d]imidazol-4-(1H)-one,
1-Propyl-[1]benzothiopyrano[3,4-d]imidazol-4-(1H)-one,
1-Ethyl-[1]benzothiopyrano[3,4-d]imidazol-4-(1H)-one,
1-Methyl-[1]benzothiopyrano[3,4-d]imidazol-4-(1H)-one,
[1]Benzothiopyrano[3,4-d]imidazol-4-(1H)-one,
2-Methyl-[1]benzothiopyrano[3,4-d]imidazol-4-(1H)-one,
1-(2-Chlorophenyl-[1]benzopyrano[3,4-d]imidazol-4-(1H)-one,
1-(4-Methyl-phenyl)-[1]benzopyrano[3,4-d]imidazol-4-(1H)-one,
1-(4-Fluorophenyl)-[1]benzopyrano[3,4-d]imidazol-4-(1H)-one,
1-(2,4-Dimethyl-phenyl)-[1]benzopyrano[3,4-d]imidazol-4-(1H)-one,
1-(3-Chlorophenyl)-[1]benzopyrano[3,4-d]imidazol-4-(1H)-one,
1-(2,4-Dichlorophenyl)-[1]benzopyrano[3,4-d]imidazol-4-(1H)-one,
1-(2,5-Dichlorophenyl)-[1]benzopyrano[3,4-d]imidazol-4-(1H)-one,
1-(4-Acetamido-phenyl)-[1]benzopyrano[3,4-d]imidazol-4-(1H)-one,
1-(2-Fluorophenyl)-[1]benzopyrano[3,4-d]imidazol-4-(1H)-one,
1-(3-Fluorophenyl)-[1]benzopyrano[3,4-d]imidazol-4-(1H)-one,
1-(2-Benzyloxy-phenyl)-[1]benzopyrano[3,4-d]imidazol-4-(1H)-one,
1-(2,6-Dimethyl-phenyl)-[1]benzopyrano[3,4-d]imidazol-4-(1H)-one, 1-(Indian-5-yl)-[1]benzopyrano[3,4-d]imidazol-4-(1H)-one,
1-(2-Methoxy-phenyl)-[1]benzopyrano[3,4-d]imidazol-4-(1H)-one,
1-(2,3-Dimethyl-phenyl)-[1]benzopyrano[3,4-d]imidazol-(1H)-4-one,
1-(2,3-Dichlorophenyl)-[1]benzopyrano[3,4-d]imidazol-4-(1H)-one,
1-(3-Chloro-4-methyl-phenyl)-[1]benzopyrano[3,4-d]imidazol-4-(1H)-one,
1-(2,5-Dimethyl-phenyl)-[1]benzopyrano[3,4-d]imidazol-4-(1H)-one,
1-(4-Chlorophenyl)-[1]benzopyrano[3,4-d]imidazol-4-(1H)-one,
1-(1,2,3,4-Tetrahydronaphthalen-5-yl)-[1]benzopyrano[3,4-d]imidazol-4-(1H)-one,
1-(Dibenzothien-2-yl)-[1]benzopyrano[3,4-d]imidazol-4-(1H)-one,
1-(3-Methoxy-phenyl)-[1]benzopyrano[3,4-d]imidazol-4-(1H)-one, or
1-(4-Carboxy-2-methyl-phenyl)-[1]benzopyrano[3,4-d]imidazol-4-(1H)-one.

\* \* \* \* \*

UNITED STATES PATENT AND TRADEMARK OFFICE
CERTIFICATE OF CORRECTION

PATENT NO.         : 7,491,742 B2                                                Page 1 of 1
APPLICATION NO. : 10/750878
DATED              : February 17, 2009
INVENTOR(S)        : Hans-Michael Eggenweiler et al.

It is certified that error appears in the above-identified patent and that said Letters Patent is hereby corrected as shown below:

On the title page, include item (30), Foreign Application Priority Data: --Oct. 21, 1999 (DE)......199 50 647--

Column 9, line 1, reads "1-(Indian-5-yl)..." should read --1-(Indan-5-yl)...--

Signed and Sealed this

Fifteenth Day of September, 2009

David J. Kappos
*Director of the United States Patent and Trademark Office*